(12) United States Patent
Tenger et al.

(10) Patent No.: US 8,012,087 B2
(45) Date of Patent: *Sep. 6, 2011

(54) LARYNGOSCOPE BLADE AND METHOD OF USE

(75) Inventors: James P. Tenger, Carlsbad, CA (US); Leslie A. Tenger, Carlsbad, CA (US); John R. Hicks, Carlsbad, CA (US)

(73) Assignee: Intubrite, LLC, Rancho Santa Fe, CA (US)

( * ) Notice: Subject to any disclaimer, the term of this patent is extended or adjusted under 35 U.S.C. 154(b) by 593 days.

This patent is subject to a terminal disclaimer.

(21) Appl. No.: 12/173,961

(22) Filed: Jul. 16, 2008

(65) Prior Publication Data

US 2009/0318767 A1    Dec. 24, 2009

Related U.S. Application Data

(63) Continuation-in-part of application No. 12/144,147, filed on Jun. 23, 2008.

(51) Int. Cl.
*A61B 1/267* (2006.01)

(52) U.S. Cl. ........ 600/199; 600/185; 600/193; 600/241; 600/245

(58) Field of Classification Search .......... 600/185–199, 600/223, 245
See application file for complete search history.

(56) References Cited

U.S. PATENT DOCUMENTS

| | | | |
|---|---|---|---|
| 4,782,819 A | | 11/1988 | Adair |
| 4,827,910 A | | 5/1989 | Mathews, III |
| 5,165,387 A | * | 11/1992 | Woodson ............... 600/184 |
| 5,645,116 A | * | 7/1997 | McDonald ............. 141/208 |
| 6,459,919 B1 | | 10/2002 | Lys et al. |
| 6,569,089 B1 | | 5/2003 | Covington et al. |
| 6,809,499 B2 | | 10/2004 | Solingen |
| 6,876,446 B2 | * | 4/2005 | Taylor et al. .......... 356/241.1 |
| 6,974,239 B2 | * | 12/2005 | Currie et al. .......... 362/558 |
| 7,052,456 B2 | | 5/2006 | Simon |
| 7,308,296 B2 | | 12/2007 | Lys et al. |
| 2002/0087050 A1 | * | 7/2002 | Rudischhauser et al. ..... 600/199 |
| 2003/0191459 A1 | | 10/2003 | Ganz et al. |

(Continued)

FOREIGN PATENT DOCUMENTS

KR    1020070044379    4/2007

(Continued)

OTHER PUBLICATIONS

ISO 21348, Space Environment (natural and artificial)—Process for determining solar irradiances, 2007, ISO 21348:2007(E).*

(Continued)

*Primary Examiner* — Eduardo C Robert
*Assistant Examiner* — Paul J Spatafore
(74) *Attorney, Agent, or Firm* — Stephen C. Beuerle; Procopio Cory Hargreaves & Savitch LLP (57) ABSTRACT

A laryngoscope blade for use in viewing the vocal cords of a patient in performance of an endotracheal intubation includes a laryngoscope blade portion connectable to a laryngoscope handle to lift the patient's tongue and mandible for viewing the vocal cords and aid in the insertion of an endotracheal tube; and a black light source carried by the blade portion to prompt the visible effects of fluorescence and phosphorescence with respect to the patient's vocal cords for viewing the vocal cords and passing of the endotracheal tube there between during endotracheal intubation.

7 Claims, 5 Drawing Sheets

U.S. PATENT DOCUMENTS

| | | | |
|---|---|---|---|
| 2003/0195390 A1 | 10/2003 | Graumann | |
| 2006/0030880 A1* | 2/2006 | Tylke | 606/205 |
| 2006/0069314 A1* | 3/2006 | Farr | 600/179 |
| 2006/0241347 A1* | 10/2006 | Whitehead | 600/146 |
| 2007/0112257 A1* | 5/2007 | Hensler | 600/199 |
| 2007/0156022 A1* | 7/2007 | Patel | 600/199 |
| 2007/0183145 A1* | 8/2007 | Yu | 362/201 |
| 2007/0232862 A1* | 10/2007 | Herman | 600/190 |
| 2007/0276185 A1 | 11/2007 | Gono et al. | |
| 2007/0276191 A1 | 11/2007 | Selover et al. | |
| 2008/0015560 A1 | 1/2008 | Gowda et al. | |
| 2008/0045800 A2 | 2/2008 | Farr | |
| 2008/0045801 A1* | 2/2008 | Shalman et al. | 600/193 |
| 2008/0300475 A1* | 12/2008 | Jaeger et al. | 600/364 |
| 2009/0076334 A1* | 3/2009 | Chen | 600/223 |
| 2009/0187078 A1* | 7/2009 | Dunlop | 600/179 |

FOREIGN PATENT DOCUMENTS

WO  93/11700  6/1993

OTHER PUBLICATIONS

Walsh, Laurence J. and Shakibaie, Fardad, Ultraviolet-induced fluorescence: shedding new light on dental biofilms and dental carries, Nov./Dec. 2007, Australasian Dental Practice, pp. 56-58.*

Notification, International Search Report and Written Opinion dated Oct. 5, 2010 for PCT/US2010/023194.

International Search Report and Written Opinion for PCT/US08/074878, dated Mar. 19, 2009.

* cited by examiner

LARYNGOSCOPE BLADE AND METHOD OF USE

CROSS-REFERENCE TO RELATED APPLICATIONS

This application is a continuation-in-part of U.S. patent application Ser. No. 12/144,147, filed on Jun. 23, 2008, which is incorporated by reference herein as thought set forth in full.

FIELD OF THE INVENTION

The field of this invention relates to laryngoscopes and the laryngoscopy procedure.

BACKGROUND OF THE INVENTION

Health care providers perform direct laryngoscopy to either clear a patient's airway of debris, or place an endotracheal tube into a patient's trachea to assist or replace a patient's ability to oxygenate his/her system. The laryngoscope utilizes either a lighted straight or curved blade that allows visualization of the vocal cords, indicating the opening of the trachea. This lighted blade is used to keep the tongue from obstructing the medical provider's view of the vocal cords. The tip of the blade lifts the epiglottis, thereby providing a direct view into the patient's trachea, and reducing the risk of intubating the esophagus instead. Laryngoscopes in the past have used halogen or LED bulbs to provide a white light source on the laryngoscope blade to illuminate the vocal cords during laryngoscopy. Even with a light source on the laryngoscope blade, viewing of the vocal cords has still proven difficult during laryngoscopy. Accordingly, without the ability to view the vocal cords, many possible laryngoscopy procedures are not performed successfully, resulting in additional harm or death for the patient.

SUMMARY OF THE INVENTION

To solve these problems and others, an aspect of present invention involves a laryngoscope including an improved light source. The laryngoscope blade carries a black light source that emits a black light during laryngoscopy. The black light enhances visualization of the vocal cords so that visualization of the endotracheal tube passing through the vocal cords is enhanced. The black light emitted from the laryngoscope enhances colors that are white and/or contain phosphors in the region of the vocal cords, enhancing visualization of the target vocal cords. In another implementation of the laryngoscope, the laryngoscope blade carries a black light source and a white light source. A switch on the laryngoscope enables the health care provide to actuate the black light source, the white light source, or to activate both light sources.

An additional aspect of the invention involves a laryngoscope for use in viewing the vocal cords of a patient in performance of an endotracheal intubation. The laryngoscope includes a handle to be gripped by a medical professional in performing the endotracheal intubation; a blade portion extending from the handle to lift the patient's tongue and mandible for viewing the vocal cords and aid in the insertion of an endotracheal tube; a power source; and a black light source powered by the power source and carried by the blade portion to prompt the visible effects of fluorescence and phosphorescence with respect to the patient's vocal cords for viewing the vocal cords and passing of the endotracheal tube there between during endotracheal intubation.

Another aspect of the invention involves an endotracheal intubation system for performing an endotracheal intubation including the laryngoscope described immediately above; and an endotracheal tube insertable into the patient's mouth, between the patient's vocal cords into the patient's larynx, and into the patient's trachea for opening the patient's airway.

A further aspect of the invention involves a method of performing an endotracheal intubation including using the laryngoscope described immediately above to lift the patient's tongue and mandible for viewing the vocal cords and aid in the insertion of an endotracheal tube; illuminating the patient's vocal cords with the black light source to prompt the visible effects of fluorescence and phosphorescence with respect to the patient's vocal cords for viewing the vocal cords; and simultaneously visualizing the patient's vocal cords with the black light source and sliding the endotracheal tube between the patient's vocal cords and into the patient's larynx and trachea.

A still further aspect of the invention involves a laryngoscope blade for use in viewing the vocal cords of a patient in performance of an endotracheal intubation. The laryngoscope blade includes a laryngoscope blade portion connectable to a laryngoscope handle to lift the patient's tongue and mandible for viewing the vocal cords and aid in the insertion of an endotracheal tube; and a black light source carried by the blade portion to prompt the visible effects of fluorescence and phosphorescence with respect to the patient's vocal cords for viewing the vocal cords and passing of the endotracheal tube there between during endotracheal intubation.

Further objects and advantages will be apparent to those skilled in the art after a review of the drawings and the detailed description of the preferred embodiments set forth below.

DETAILED DESCRIPTION OF PREFERRED EMBODIMENTS

Figure 1:
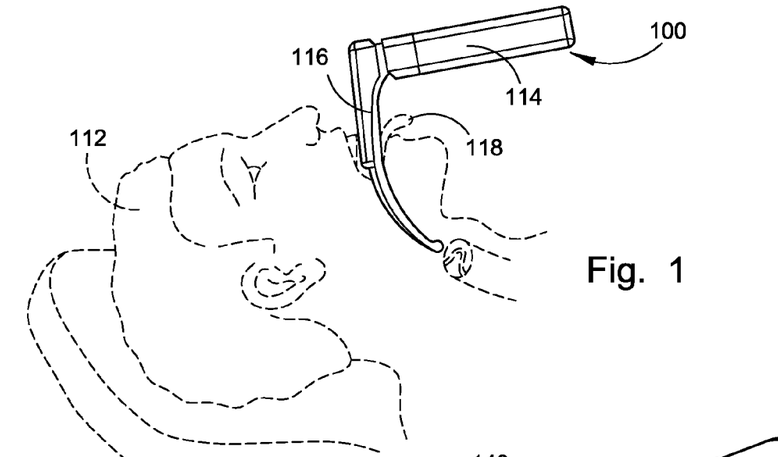
FIG. 1 is a schematic depiction of a laryngoscope being used to view a patient's larynx.
Figures 2, 3A, 3B:
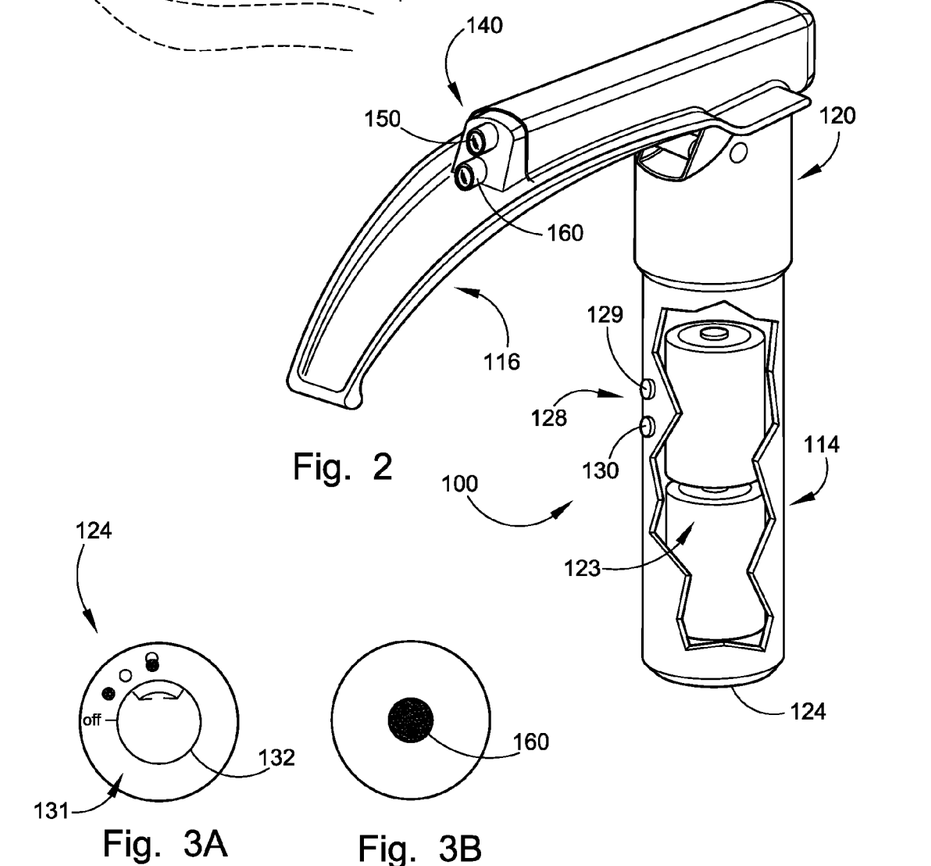
FIG. 2 is a perspective view of a laryngoscope in accordance with an embodiment of the present invention.
FIG. 3A is a bottom plan view of the laryngoscope of FIG. 2, and illustrates an embodiment of a switch that may be used with the of the laryngoscope of FIG. 2.
FIG. 3B is a bottom plan view of an alternative embodiment of a laryngoscope, and illustrates an embodiment of a black light source on the bottom of the laryngoscope.

With reference to FIGS. 1 and 2, a laryngoscope 100 constructed in accordance with an embodiment of the invention will be described. In FIG. 1, the laryngoscope 100 is shown placed in the mouth of a patient 112 for viewing the vocal cords adjacent the larynx and to aid in the insertion of an endotracheal tube 200 (FIG. 4) past the vocal cords. The laryngoscope 100 includes a handle or handgrip 114 and a blade portion 116, the latter being used to lift the tongue and mandible 118 out of the way for viewing the vocal cords.

As shown in FIG. 2, the blade portion 116 is pivotally connected to a handle cap 120. The blade portion 116, the handle cap 120, and the handle 114 can be readily assembled together for use. In the embodiment shown, when assembled, a white light source 150 and a black light source 160 are automatically actuated. In an alternative embodiment, the blade portion 116 is directly connected to a top of the handle 114 (i.e., there is no handle cap). The handle 114 is essentially a hollow tube having a closed lower or outer end 122 (FIG. 3) and an open upper end. The handle cap 120 is removably secured to an open upper end of the handle 114. A power source 123 (e.g., one or more dry cell batteries) is located within the handle cavity to provide power for light source(s) to be described.

A side of the handle 114 includes a switch 128 in the form of two pressure/push buttons 129, 130 interconnected with the power source 123, the white light source 150, and the black light source 160 that, when pressed (e.g., by a user's thumb), deactivate the respective light sources 150, 160. When the laryngoscope 100 is clicked together/assembled, both light sources 150, 160 are placed in electrical communication with the power source 123 and are automatically turned on. In the embodiment shown, push button ("white light button") 129 controls the white light source 150 so that pushing on the white light button 129 turns off the white light source 150 and push button ("black light button") 130 controls the black light source 160 so that pushing on the black light button 130 turns off the black light source 160. Thus, by applying pressure to the push buttons 129, 130, the respective light sources 150, 160 are turned off. Removing the pressure to the push buttons 129, 130 causes the respective light sources 150, 160 to be turned back on. Accordingly, the switch 128 enables the laryngoscope 100 to be switched between at least a "both on" condition where both black light is emitted from the black light source 160 and white light is emitted from the white light source 150, a black light condition where black light is emitted from the black light source 160 and the white light source 150 is off, and a white light condition where white light is emitted from the white light source 150 and the black light source 160 is off.

With reference to FIG. 3, an alternative embodiment of a switch 131 located on a bottom 124 of the handle 114 is shown. The switch 131 cooperates with electronics in the laryngoscope 100 for switching between an "off" condition, a black light condition, a white light condition, and a "both on" condition. In the embodiment shown, the switch 131 is a rotating switch with a rotating knob 132 that rotates between different positions to actuate the above conditions.

In alternative embodiments, other types of switches may be used (e.g., push-button switch, a toggle switch) on the bottom 124 of the handle 114 (or at other locations on the laryngoscope 100) to switch between an "off" condition and one or more of a black light condition, a white light condition, and a "both on" condition. In alternative embodiments, the switch 128, 131 may switch between conditions in addition to or other than an "off" condition, a black light condition, a white light condition, and a "both on" condition. For example, in an alternative embodiment, where the laryngoscope 100 includes only a black light source 160, the switch 128, 131 may switch the laryngoscope 100 between an "off" condition and a black light condition.

One or more light sources 140 are interconnected with the power source 123 in the handle 114. In the embodiment shown, as discussed above, the one or more light sources 140 include two light sources: 1) a white light source 150, and 2) a black light source 160. Example white light sources 150 include, but not by way of limitation, a white halogen light, a white incandescent light, and a white LED. The black light source 160 emits long wave UVA radiation and very little visible light. The black light source is a lamp emitting electromagnetic radiation that is almost exclusively in the soft near ultraviolet range. The black light source 160 prompts the visible effects of fluorescence and phosphorescence with respect to the patient's vocal cords and the glottis, which is the space between the vocal cords, during laryngoscopy. The black light source 160 may be a Wood's light made using Wood's glass, which is a nickel-oxide-doped glass, which blocks substantially all visible light above 400 nanometers. In alternative embodiments, other black light sources 160 (e.g., LED(s)) may be used. Preferably, the black light source 160 emits electromagnetic radiation including a wavelength in the range of 315 to 400 nm, with out emitting substantial electromagnetic radiation including a wavelength outside of the range of 315 to 400 nm. In a most preferred embodiment, the black light source 160 includes a wavelength of about 365 nm.

In the embodiment shown, the blade portion 116 is a curved Macintosh blade; however, in alternative embodiments, other types of blades (e.g., straight Miller/Robertshaw blade) may be used. The blade portion 116 carries the one or more light sources 140. Although the one or more light sources 140 are shown on a top of the blade portion 116, in alternative embodiments, the one or more light sources 140 are disposed at one or more of the following locations: a side of the blade portion 116, a bottom of the blade portion 116, a top of the blade portion 116, a distal tip of the blade portion 116, and other locations on or relative to the blade portion 116.

With reference to FIG. 3B, in a further embodiment, in addition to or instead of the one or more light sources 140 being carried by the blade portion 116, a black light source (e.g., black light source 160) is carried by the bottom 124 of the handle 114 for emitting black light from the bottom 124 of the handle 114. In such an embodiment, a switch (e.g., switch 128) for controlling the black light source on the bottom 124 of the handle 114 is preferably located in a location other than the bottom 124 of the handle 114.

Figure 4:
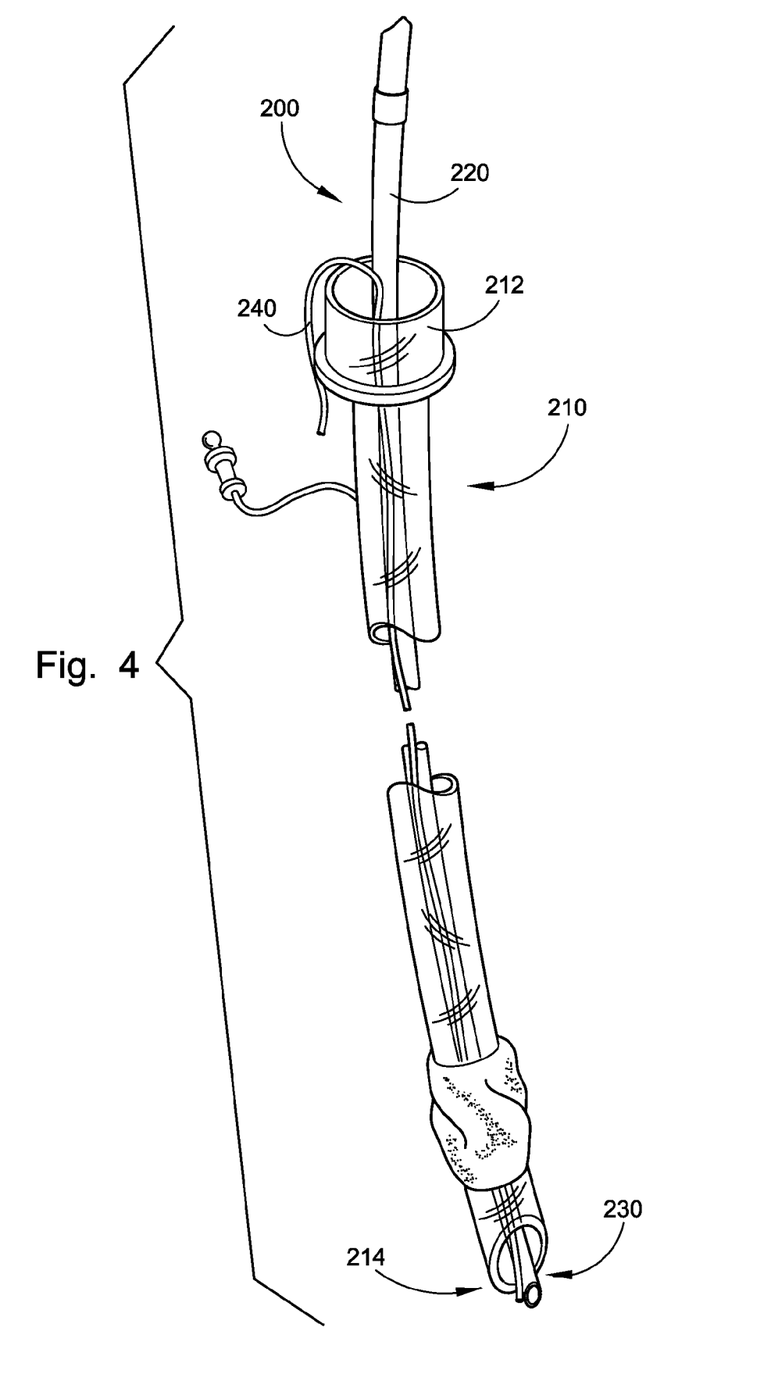
FIG. 4 is an embodiment of an endotracheal tube that may be used with the laryngoscope of FIGS. 1-3.

With reference to FIG. 4, an embodiment of an endotracheal tube 200 that may be used with the laryngoscope 100 (as part of an endotracheal intubation system) in performing endotracheal intubation will be described. The endotracheal tube 200 includes a clear plastic intubation tube 210 with an elongated central lumen. The intubation tube 210 includes a larger-diameter open upper end 212, which may include a cap, and a pointed open lower end or tip 214. An elongated scope (e.g., a fiberoptic scope) 220 may be received within the lumen of the intubation tube 210. The scope 220 includes a distal viewing tip 230. A plastic transparent holding sheath may cover the scope 220. A longitudinally built-in narrow malleable metal intubation stylet 240, which is a narrow piece of flat metal, may be built into the holding sheath and adhered to an outer wall of the holding sheath for controlling the geometry/shape of the scope 220/endotracheal tube 200 to match the physiology/anatomy of the patient during endotracheal intubation.

In an alternative embodiment, one or more of the intubation tube 210 and the stylet 240 include a fluorescent color or other color/substance that is enhanced by the black light or that reacts to the black light (on the entire tube 210/stylet 240 or a portion and/or component there of).

A method of performing endotracheal intubation using the laryngoscope 100 and the endotracheal tube 200 will be described. The black light source 160 of the laryngoscope 100 is activated (e.g., when the laryngoscope 100 is clicked together/assembled. The blade portion 160 of the laryngoscope 100 is inserted into the patient's mouth and behind the patient's tongue and mandible 118. By gripping the handle 114 with one's hand, the tongue and mandible 118 are lifted for viewing the vocal cords adjacent the larynx and to aid in the insertion of the endotracheal tube 200 past the vocal cords. The black light emitted from the laryngoscope 100 prompts the visible effects of fluorescence and phosphorescence with respect to the patient's vocal cords and the glottis, making the patient's vocal cords and the glottis visible either directly by the eyes of the medical provider or via the scope 220 of the endotracheal tube 200. The endotracheal tube 200 is inserted into the patient's mouth, between the patient's visible vocal cords into the larynx, and then into the trachea of the patient in a usual manner. The stylet 200 of the endotracheal tube 200 may be used to shape the scope 220/endotracheal tube 200 to the individual anatomy/pathology of the patient.

As discussed above, in the embodiment of the laryngoscope 100 shown in FIG. 1, applying pressure to the push buttons 129, 130 causes the respective light sources 150, 160 to be deactivated and removing the pressure to the push buttons 129, 130 causes the respective light sources 150, 160 to be re-activated. The medical provider operates the push buttons 129, 130 of the switch 128 (e.g., to cause only black light to be emitted, only white light to be emitted, or both types of light to be emitted) so that optimal viewing of the vocal cords occurs. The medical provider may prefer to use the black light condition and/or the white light condition, depending on external lighting conditions, the individual anatomy/pathology of the patient, the patient's condition, and other factors.

Figure 5:
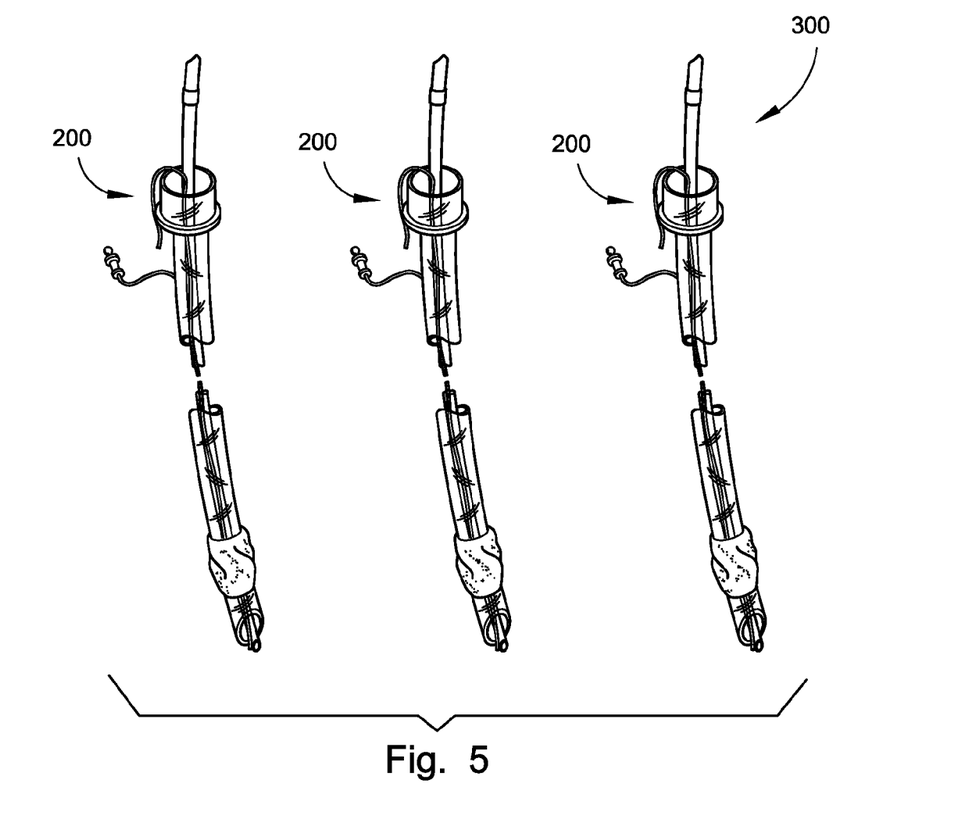
FIG. 5 is an embodiment of a kit of endotracheal tubes that may be used with the laryngoscope of FIGS. 1-3.

With reference to FIG. 5, in another embodiment of the above endotracheal tube 200, a kit 300 of endotracheal tubes 200, intubation tubes 210, and/or stylets 240 of different sizes (e.g., different weight, height, and/or depth; adult version, pediatric version) are color-coded with different fluorescent colors or other color/substance that is enhanced by the black light or that reacts to the black light. For example, but not by way of limitation, the intubation tube 210 of each different endotracheal tube 200 is coated with a unique fluorescent colored material or other color/substance that is enhanced by the black light or that reacts to the black light. The entire endotracheal tube 200 may include a fluorescent color or one or more portions of the endotracheal tube 200 may include one or more fluorescent colors (or other color/substance that is enhanced by the black light or that reacts to the black light). For example, but not by way of limitation, a cap of the endotracheal tube 200 may include a unique fluorescent color (or other color/substance), the intubation tube 210 may include a unique fluorescent color (or other color/substance), and/or the stylet 240 may include a unique fluorescent color (or other color/substance) for identifying the proper size endotracheal tube 200, intubation tube 210, and/or stylet 240, and for improving visualization of the endotracheal tube 200, intubation tube 210, and/or stylet 240 during endotracheal intubation. Using the black light source 160 of the laryngoscope 100, one may easily identify the correct-sized endotracheal tube 200, intubation tube 210, and/or stylet 240 by shining black light on the kit of endotracheal tubes 200, intubation tubes 210, and/or stylets 240 identified by different fluorescent colors (or other color/substance) so that the proper-sized endotracheal tube 200, intubation tube 210, and/or stylet 240 for the patient/application is selected. The different-size/fluorescent-color endotracheal tubes 200, intubation tubes 210, and/or stylets 240 are easy to identify with a black light source, especially in no-light, low-light, or dark conditions. Further, the fluorescent (or other color/substance) endotracheal tube 200, intubation tube 210, and/or stylet 240, in combination with the black light laryngoscope 100, improves visualization of the endotracheal tube 200, intubation tube 210, and/or stylet 240 passing the vocal cords during endotracheal intubation.

Figure 6:
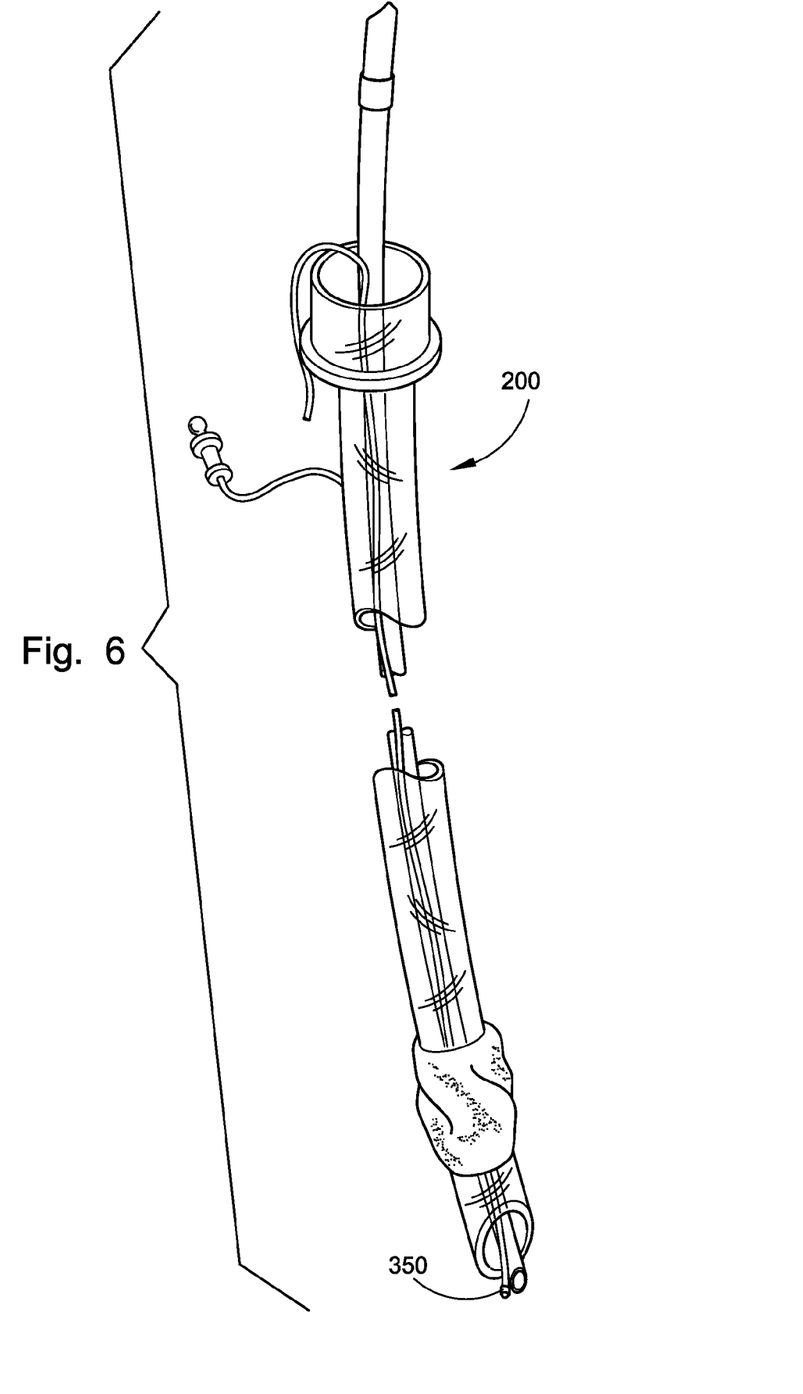
FIG. 6 is an alternative embodiment of an endotracheal tube that may be used with the laryngoscope of FIGS. 1-3 or a standard laryngoscope.

With reference to FIG. 6, in another embodiment, the stylet 240 and/or the endotracheal tube 200 includes a black light source 350 that emits black light to enhance visualization of the vocal cords during endotracheal intubation. For example, the stylet 240 and/or the endotracheal tube 200 with black light source 250 may be used in conjunction with the laryngoscope 100 discussed above with respect to FIGS. 1-3, or in conjunction with a normal laryngoscope that does not have a black light source 150.

Figure 7:
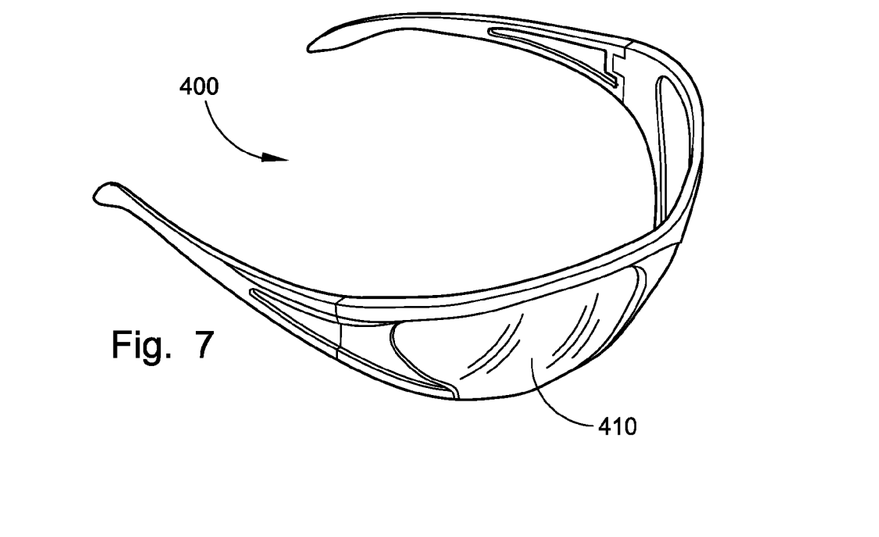
FIG. 7 is an embodiment of a pair of protection intubation glasses that may be used with the laryngoscope of FIGS. 1-3 and/or the endotracheal tube(s) of FIGS. 4-6.

With reference to FIG. 7, an embodiment of a pair of protection intubation glasses 400 includes lenses 410 configured (e.g., tinted to a particular shade) so that when used in conjunction with the black light sources described above during endotracheal intubation, the visibility of the vocal cords is intensified/enhanced.

Figures 8, 9:
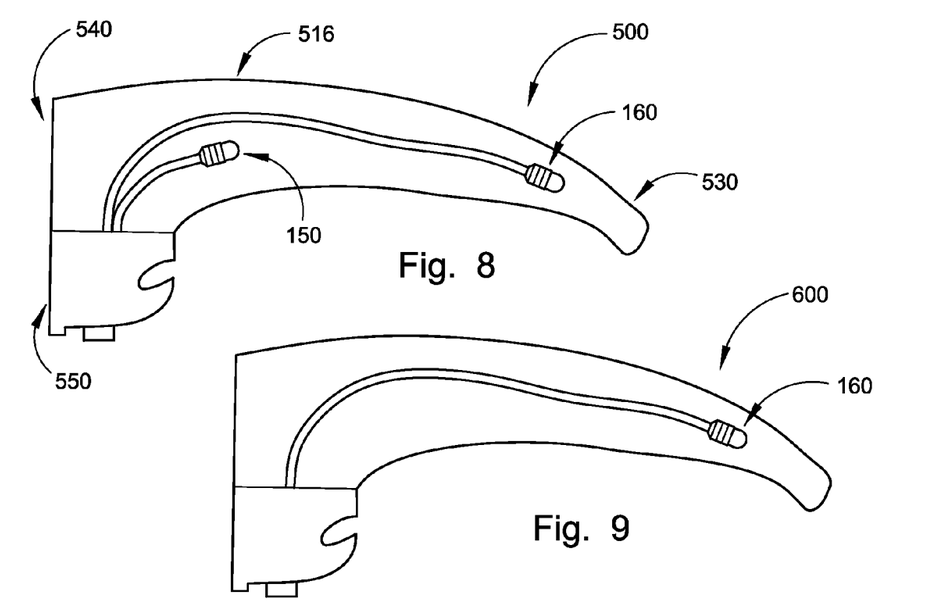
FIG. 8 is a side-elevational view of a separate laryngoscope blade in accordance with an embodiment of the present invention.
FIG. 9 is a side-elevational view of a separate laryngoscope blade in accordance with another embodiment of the present invention.

With reference to FIG. 8, an embodiment of a separate laryngoscope blade 500 that may be detachably connected to a separate laryngoscope handle (e.g., handle 114) will be described. In the embodiment shown, the blade 500 is a curved Macintosh blade; however, in alternative embodiments, other types of blades (e.g., straight Miller/Robertshaw blade) may be used.

The blade 500 may be made of stainless steel, plastic, or a combination of stainless steel and plastic. In other embodiments, other materials are used.

The blade 500 includes a blade portion 516 with a distal portion 530 and a proximal portion 540. The blade portion 516 carries a white light source 150 and a black light source 160. The black light source 160 is located distally of (i.e., closer to the distal portion 530 relative to) the white light source 150 on the blade portion 516. The advantage of locating the black light source 160 distally of the white light source 150 is that, in use, the proximal white light source 150 provides general illumination (e.g., of the interior of the mouth and back of the patient's throat) while the distal black light source 160, which is disposed closer to the patient's vocal cords and the glottis, provides directed black light illumination of the patient's vocal cords and the glottis, prompting the visible effects of fluorescence and phosphorescence with respect to the patient's vocal cords and the glottis. In alternative embodiments, the white light source 150 and/or the black light source 160 are located at other positions/locations than those shown.

The blade 500 includes a connection section 550 for mechanically coupling the blade 500 to a top of the separate laryngoscope handle and electrically coupling the white light source 150 and the black light source 160 to a power source in the laryngoscope handle. Alternatively, the blade 500 carries its own power source for powering the white light source 150 and the black light source 160. When the blade 500 is connected to the laryngoscope handle, the connection section 550 is configured so that both the white light source 150 and the black light source 160 are automatically activated and when the blade 500 is disconnected to the laryngoscope handle, the white light source 150 and the black light source 160 are automatically deactivated. This automatic activation/deactivation may be achieved by electrical connectors and/or switch(es). For example, the mechanical connection between the connection section 550 and the laryngoscope handle may put the power source in the handle in electrical communication with the white light source 150 and the black light source 160 or may cause a switch at the interface of the connection section 550 and the laryngoscope handle to be closed. In an alternative embodiment, the blade 500 and/or laryngoscope handle carries a user controllable switch to control activation/deactivation of the white light source 150 and the black light source 160 (e.g., both on, both off, one on and one off).

FIG. 9 illustrates another embodiment of a separate laryngoscope blade 600 that is the same as the blade 500, except the blade 600 includes only a black light source 160 instead of both a white light source 150 and a black light source 160.

Figure 10:
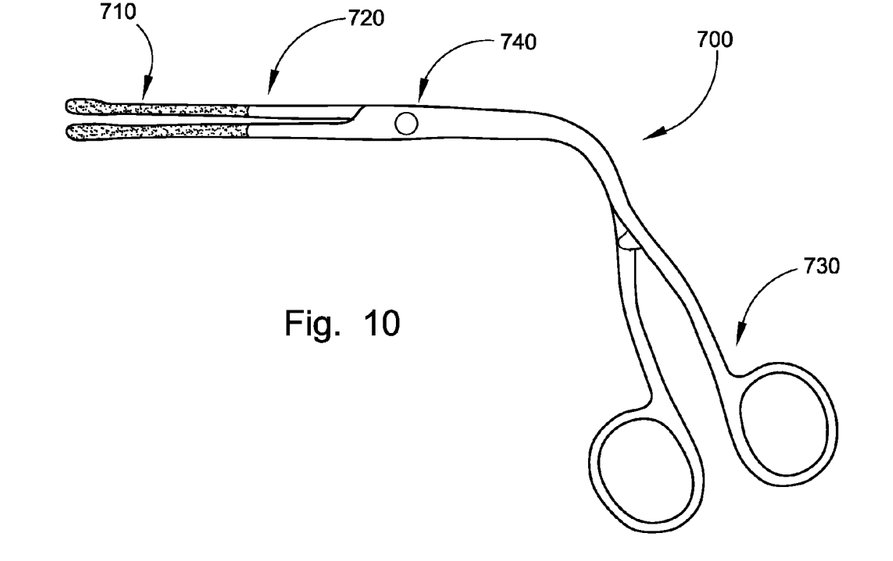
FIG. 10 is a side-elevational view of an embodiment of a pair of forceps.

With reference to FIG. 10, an embodiment of a pair of forceps 700 including distal portions 710 of jaws 720 coated with a fluorescent colored material/substance (or other color/substance) that is enhanced by the black light or that reacts to the black light is shown. The forceps 700 include a handle 730 at a proximal end and the distal jaws 720 at an opposite end for gripping an object. The forceps 700 pivot about a pivot section 740. In use, the forceps 700 are used to grip an object (e.g., to remove an object from the patient's body). Black light (e.g., from any of the black light devices described above and shown herein) is directed at the object and the jaws 720 of the forceps 700. The fluorescent colored material/substance is enhanced by the black light, allowing the user to see exactly where to grab the object and, most importantly, not cause damage to surrounding tissue. The user then grabs the object with the jaws 720 of the forceps 700 and, if appropriate, removes the object from the patient's body. Although the forceps 700 in the embodiment shown are Magill-type forceps, in alternative embodiments, other types of forceps with jaws 720 coated with a fluorescent material/substance may be used.

The above figures may depict exemplary configurations for the invention, which is done to aid in understanding the features and functionality that can be included in the invention. The invention is not restricted to the illustrated architectures or configurations, but can be implemented using a variety of alternative architectures and configurations. Additionally, although the invention is described above in terms of various exemplary embodiments and implementations, it should be understood that the various features and functionality described in one or more of the individual embodiments with which they are described, but instead can be applied, alone or in some combination, to one or more of the other embodiments of the invention, whether or not such embodiments are described and whether or not such features are presented as being a part of a described embodiment. Thus the breadth and scope of the present invention, especially in the following claims, should not be limited by any of the above-described exemplary embodiments.

Terms and phrases used in this document, and variations thereof, unless otherwise expressly stated, should be construed as open ended as opposed to limiting. As examples of the foregoing: the term "including" should be read as mean "including, without limitation" or the like; the term "example" is used to provide exemplary instances of the item in discussion, not an exhaustive or limiting list thereof; and adjectives such as "conventional," "traditional," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although item, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

We claim:

1. A laryngoscope blade for use in viewing the vocal cords of a patient in performance of an endotracheal intubation, comprising:
   a laryngoscope blade portion connectable to a laryngoscope handle to lift the patient's tongue and mandible for viewing the vocal cords and aid in the insertion of an endotracheal tube, the blade portion including a proximal portion and a distal portion; and
   one or more light sources carried by the blade portion and including a light source closer to the distal portion of the blade portion and a light source closer to the proximal portion of the blade portion, the one or more light sources comprising:
      a black light source carried by the blade portion to prompt the visible effects of fluorescence and phosphorescence with respect to the patient's vocal cords for viewing the vocal cords and surrounding anatomy and passing of the endotracheal tube there between during endotracheal intubation; and
      a white light source carried by the blade portion to provide general illumination of the interior of the patient's mouth and back of the patient's throat.

2. The laryngoscope blade of claim 1, wherein the black light source emits long wave UVA radiation in the soft near ultraviolet range.

3. The laryngoscope blade of claim 1, wherein the black light source emits electromagnetic radiation having a wavelength in the range of 315-400 nm without emitting substantial electromagnetic radiation having a wavelength outside of 315-400 nm.

4. The laryngoscope blade of claim 1, wherein the laryngoscope blade includes a connection section for detachably connecting the laryngoscope blade to a laryngoscope handle.

5. The laryngoscope blade of claim 4, wherein the connection section is configured to cause the black light source to be automatically activated when the connection section is attached to the laryngoscope handle and automatically deactivated when the connection section is detached from the laryngoscope handle.

6. The laryngoscope blade of claim 1, further including forceps including a handle and jaws, the jaws including a fluorescent-colored substance.

7. A method of performing an endotracheal intubation, comprising:
   assembling a laryngoscope by connecting the laryngoscope blade of claim 1 to a laryngoscope handle;

using the laryngoscope to lift the patient's tongue and mandible for viewing the vocal cords and aid in the insertion of an endotracheal tube;

providing the black light source and the white light source in a both on condition for simultaneously performing the following:

illuminating the patient's vocal cords with the black light source to prompt the visible effects of fluorescence and phosphorescence with respect to the patient's vocal cords for viewing the vocal cords and surrounding anatomy, and     providing general illumination with the white light source of the interior of the patient's mouth and back of the patient's throat;

simultaneously visualizing the patient's vocal cords with the black light source and sliding the endotracheal tube between the patient's vocal cords and into the patient's larynx and trachea.

\* \* \* \* \*